United States Patent [19]

Shuster et al.

[11] Patent Number: 4,472,378

[45] Date of Patent: Sep. 18, 1984

[54] LIVE VACCINE FOR THE PREVENTION OF SALMONELLOSIS IN WATER FOWL, A PROCESS FOR MAKING AND APPLYING THE SAME

[76] Inventors: Boris J. Shuster, Vostrya kovsky proezd, 3, korpus 1, kv. 13; Jury A. Malakhov, Veshnya kovskaya ulitsa, 27, korpus 2, kv. 57, both of Moscow; Fedor S. Kirzhaev, ulitsa Pobedy, 23, kv. 9, Leningradskaya oblast, Lomonosov; Arkady S. Persov, ulitsa Pobedy, 21a, kv. 58, Leningradskaya oblast, Lomonosov; Vladimir A. Sedov, Polimernaya ulitsa, 7, kv. 120, Moscow; Anatoly M. Kosikov, ulitsa Artema, 7a, kv. 14, Stavropol; Vyacheslav N. Guschin, Kubinka, 10, kv. 31; Vladimir G. Likhoded, Smolenskaya ulitsa, 10, kv. 32, both of Moscow, all of U.S.S.R.

[21] Appl. No.: 445,272

[22] Filed: Nov. 29, 1982

[51] Int. Cl.$^3$ ...................... A61K 39/112; C12N 1/20
[52] U.S. Cl. ....................................... 424/92; 435/253
[58] Field of Search ..................... 424/92, 93; 435/253

[56] References Cited

U.S. PATENT DOCUMENTS 4,350,684  9/1982  Pardon et al. ....................... 424/92

FOREIGN PATENT DOCUMENTS 2464300  6/1981  France .

*Primary Examiner*—Blondel Hazel
*Attorney, Agent, or Firm*—Burgess, Ryan & Wayne

[57] ABSTRACT

A novel live vaccine for the prevention of salmonellosis in water fowl comprising essentially a suspension of living culture of the attenuated strain *Salmonella typhimurium* No. 3, deposited at the All-Union State Research Control Institute for Veterinary Preparations, the USSR Ministry of Agriculture (No. 121), in a concentration of 2-4 billion microbe cells per 10 cm$^3$ of drinking water. A process for making said vaccine, wherein the attenuated strain *Salmonella typhi-murium* No. 3 is cultivated in a culture medium containing sources of carbon, nitrogen, mineral salts, biologically active substances at a temperature of 37°-38° C. to produce the highest attainable accumulation of biomass during a period of 10-14 hours with subsequent drying and obtainment of the vaccine.

A method of specific prophylaxis of salmonellosis in water fowl, wherein the live vaccine is administered to the poultry twice orally at a 2-3 days interval in a dose of 2 billion microbe cells at the first, and 4 billion microbe cells at the second, feeding, being combined with drinking water.

13 Claims, No Drawings

LIVE VACCINE FOR THE PREVENTION OF SALMONELLOSIS IN WATER FOWL, A PROCESS FOR MAKING AND APPLYING THE SAME

This invention relates generally to the field of veterinary medicine, but more particularly to a novel live vaccine for the prevention of salmonellosis in water fowl, a process for making the same and its prophylactic application in water fowl to combat salmonellosis caused by *Salmonella typhi-murium*.

*S. typhi-murium* caused salmonellosis affecting water fowl is marked by high incidence, very contagious character and often fatal outcome.

Furthermore, *S. typhi-murium* has been implicated as one of the principal agents causing food toxicoinfections in man while the water fowl is the major host of the microbe in natural conditions and the products obtained from slaughtering the infested poultry constitute the basic source of infections in man.

Prevention and management of salmonellosis in water fowl relies primarily on the use of medicinal drugs and general veterinary-sanitary measures, which, as a rule, fall short of ensuring a higher health standard at the farm and maintenance of the livestock at a desired numerical level. The specific prophylaxis of salmonellosis in water fowl is extremely inadequate.

There is known a polyvalent killed vaccine used for colibacillosis and salmonellosis in fur animals, poultry calves, young pigs, which consists of a four-billion suspension of *S. typhi-murium, S. cholerae-suis, S. dublin* and *E. coli* of 24 different serotypes killed with formalin and thimerosal. The vaccine, produced as a liquid, is recommended for the subcutaneous administration repeated twice in birds: first in a dose of 0.25-0.5, and then 0.5-1.0 ml. (Veterinary statute, Moscow, "Kolos" publishers, 1973, vol. I, p. 548; manual entitled "Veterinary agents," Moscow, "Kolos" publishers, 1981, p. 223).

The vaccine exhibits a low immunogenicity. Inoculation does not confer the complete protection against disease or prevent the individual from becoming a carrier. Moreover, the vaccine contains Salmonella (*S. dublin* and *S. choleraesuis*) and Escherichia (0111, 0119, 0127, 0139, etc.), which are not pathogenic in birds. Twice repeated parenteral administration of the vaccine with a syringe is too complicated for a large scale inoculation campaign. The aforesaid vaccine poses a substantial danger of allergic reaction.

Of the greatest promise in the prevention of salmonelloses in animals are the live vaccines capable of stimulating the cellular mechanisms of immunity which play a leading role in the protection of the organism against infectious agents (Collins, Bact. Rev. 1974, 38, 4, 371-402).

Current practice makes use of the live vaccines for salmonellosis: calves of the strain *S. dublin* (U.S. Pat. No. 3,356,574 patented Dec. 5, 1967), pigs of the strain *S. cholerae-suis* (U.S. Pat. No. 3,364,117 of Jan. 16, 1968), sheep of the strain *S. abortus-ovis* (French Pat. No. 2,464,300 of Mar. 6, 1981). However, the live vaccines for salmonellosis in water fowl are not described in the literature.

An object of the invention is to provide a novel live vaccine which will be highly immunogenic, efficacious, safe and simple to manufacture, convenient in use, having a long storage life, capable of establishing a strong immunological resistance to salmonellosis in water fowl.

The object is accomplished by providing a novel live vaccine for the prevention of salmonellosis in water fowl, consisting of the suspension of a live culture prepared from the attenuated strain *Salmonella typhi-murium* No. 3 deposited at the All-Union State Research Control Institute for Veterinary Preparations, the USSR Ministry of Agriculture (No. 121), in a concentration of 2-4 billion of microbe cells per 10 cm$^3$ of drinking water. To sustain the microbe cells in viable stage, the vaccine of this invention comprises a protective medium of the following composition, in percent by weight:

saccharose: 4-12.0,
gelatin: 0.6-3.0,
water: the remainder in an amount of 1 cm$^3$ of the protective medium per 30-40 billion of living microbe cells.

What is new and useful likewise is a process for making the vaccine of this invention. The process for making the live vaccine for the prevention of salmonellosis in water fowl by means of growing the strain *Salmonella typhi-murium* in a culture medium containing sources of carbon, nitrogen, mineral salts and biologically active substances to produce the highest attainable accumulation of biomass with subsequent drying and obtainment of the vaccine, according to the invention, utilizes the strain *Salmonella typhi-murium* No. 3, deposited at the All-Union State Research Control Institute for Veterinary Preparations, the USSR Ministry of Agriculture, as the growth culture, said process of growth being effected at a temperature of 37°-38° C. for the duration of 10-14 hrs. Prior to drying the biomass is preferably mixed with a protective medium of the following composition, percent by weight: saccharose 4-12.0, gelatin 0.6-3.0, the balance being water, in an amount of 1 cm$^3$ of the protective medium per 30-40 billion of microbe cells.

The vaccine of this invention is innocuous, possesses high immunogenic potential and in oral administration can be employed as a means of specific prophylaxis against salmonellosis in water fowl, e.g. at unfavourably affected farms.

The attenuated strain *S. typhi-murium* No. 3 used to produce the vaccine is distinguished by the fact that its genome comprises two mutations which, independently of each other, act to reduce virulence and ensure a steadily low residual virulence.

The attenuated strain is characterized by the following features:

morphological features: appears as small highly motile gram-negative rod-shaped microorganisms having no spores or capsules and measuring 1.5-2 $\mu$m $\times$ 0.3-0.5 $\mu$m;

culture properties: produces a uniform clouding in the meat-peptone broth after 8-10 hours of growth at a temperature of 37° C., i.e. exhibits a growth rate somewhat less than that of the virulent Salmonella strains which produce marked clouding of the broth in 4-5 hours. On the meat-peptone agar forms transparent, circular, smooth, slightly convex colonies (S-shaped) of a fine granular structure 1-3 mm in diameter. The strain is resistant to streptomycin (300 units/ml);

Fermentation properties: ferments glucose, maltose, mannitol, arabinose, sorbite, xylose, producing acid and gas; forms H$_2$S, does not ferment saccharose, lactose, raffinose, does not curdle milk, does not dilute gelatin, does not form indole;

Antigen structure: agglutinates under the influence of the monoreceptor "O" serums: 1,4,5,12 and H-serums of the first phase (i) and second phase (1, 2).

The attenuated strain selected from the population of the streptomycin sensitive virulent strain *S. typhi-murium* No. 415 closely resembles the parent strain in morphological aspects, fermentation properties, and the antigen structure. Of the culture properties uniquely pertaining to the attentuated strain as contrasted to the epizootic variety, are a low reproduction rate and high resistance to streptomycin.

The residual virulence of the strain expressed in $LD_{50}$ for white mice weighing 14–16 g after intradermal inoculation is $8.08 \times 10^8 \pm 1.28 \times 10^8$, $LD_{50}$ of the starting (virulent) strain being $18.9 \pm 8.4$ microbe cells. Therefore, the residual virulence of the attenuated strain in white mice is $4.0 \times 10^7$ times lower than that of the starting strain.

Stability of the residual virulence has been ascertained through a series of ten passages in white mice and five passages in calves. The residual virulence of the attenuated strain did not change after repeated passages. The data are summarized in Table I.

TABLE I $LD_{50}$ of *S. typhi-murium* strains prior to and following passages

| NOS. | STRAINS | $LD_{50}$ prior to passage | $LD_{50}$ after series of 10 passages in white mice | series of 5 passages in calves |
|---|---|---|---|---|
| 1 | 2 | 3 | 4 | 5 |
| 2 | Attenuated | $8.08 \times 10^8$ | $1.0 \times 10^9$ | $7.94 \times 10^8$ |
| 3 | Virulent | 18.9 | 10 | 10 |

The difference of $LD_{50}$ value for the attenuated strain prior to and following passages is statistically negligible ($P<0.01$).

The immunogenic capacity of the attenuated strain compared to a heated vaccine prepared from the virulent strain was studied on white mice weighinhg 14–16 g subjected to a single immunization with subcutaneous dose of 1 million microbe cells. 21 days following the immunization the mice were infected with the virulent strain in doses of 0.01, 0.1, 1 and 10 thousand microbe cells assigning 10 animals per one dose. The immunogenic capacity was evaluated by the efficacy index essentially being a ratio of the $LD_{50}$ in the study group to that in the control.

The immunogenic capacity of the attenuated strain was on the average 9 times that elicited from killed cells of the virulent strain (efficacy indices 92 and 10.4, respectively).

What follows is a detailed description of the process for preparing the vaccine of this invention.

The culture is grown in reactors in a culture medium such as Hottinger's broth for 10–12 hours at a temperature of 37°–38° C., being constantly mixed (50–60 r.p.m.) and continuously aerated to produce enrichment of each liter of the culture medium with air in the proportion of 1:2.

The thus grown broth culture is precipitated by centrifuging, then diluted in 18–19 l bottles with a protective medium to a concentration of 100–120 billion microbe cells according to the visual opacity standard, placed in ampoules and dried by sublimation in vacuum, and finally sealed. The living bacteria count per 1 cm³ of the vaccine subsequent to drying is 30–40 billion.

Determination of the living Salmonella count per 1 cm³ of the vaccine is performed by the following method. Two samples, each comprising three ampoules of the vaccine, are prepared. The vaccine in ampoules is diluted to the initial volume with physiological saline solution, then mixed and evaluated for Salmonella concentration in both samples by the opacity standard. The bacterial concentration in the vaccine should be 100 billion of microbe cells per 1 cm³.

Both samples are then used to prepare tenfold dilutions with separate pipettes to $10^{-9}$ in a sterile meat-peptone broth. From the $10^{-8}$ and $10^{-9}$ dilution of both samples 0.1 cm³ provides by each are placed into five dishes with meat-peptone agar. The culture material is uniformly distributed by tilting the dish. The dishes are then placed in a thermostat at a temperature of 37° C. for a period of 24 hours, whereupon the number of grown colonies and the concentration of living Salmonellas (x) in billion per 1 cm³ are determined by the formula:

$$x = \frac{\frac{p}{q} + \frac{p_1 \cdot 10}{q_1}}{2} \cdot 10^8,$$

where x is the concentration of living Salmonellas per 1 cm³,
p is the number of colonies in all the dishes containing the $10^{-8}$ dilution,
q is the number of dishes with $10^{-8}$ dilution,
$p_1$ is the number of colonies in all the dishes containing the $10^{-9}$ dilution,
$q_1$ is the number of dishes with $10^{-9}$ dilution.

Concentration indices for each sample are summed up and divided by the number of samples, thereby arriving at the mean concentration of living Salmonellas in the vaccine, expressed in billions of microbe cells per 1 cm³.

For safety determination, the desiccated vaccine extract is dissolved in physiological salt solution to a concentration of 20 million microbe cells per 1 cm³ according to the visual opacity standard and subsequently administered to white mice weighing 16–18 g subcutaneously in the dorsal region utilizing a dose of 10 million microbe cells in a volume of 0.5 cm³. The vaccine is pronounced safe if of the original 10 mice 8 are still alive at the end of a ten day period.

The test of the vaccine's activity requires the use of three ampoules. Each ampoule with the vaccine is filled up with physiological saline solution to the starting volume. The completely dissolved vaccine is then transferred into a sterile tube, the common sample being used to prepare a dilution of the vaccine in physiological saline solution at a concentration of 300 million living bacteria per 1 cm³. 350–400 g are selected, of which number 10 individuals receive the vaccine subcutaneously into the inguinal region in a dose of 300 million living microbe cells per 1 cm³. After 14–16 days, both the immunized and 10 control guinea pigs are infected with a lethal dose of a titrated culture of the control strain *S. typhi-murium*. Observation of the experimental animals continues 10 days following the death of half of the controls. Over the period of observation all or at least 8 guinea pigs from the control group should die while of the ten immunized animals at least 8 should survive.

In use the vaccine is a suspension of microbe cells of the attenuated strain *S. typhi-murium* No. 3 in a concentration of 2-4 billion living bacteria per 10 cm$^3$ of drinking water. The vaccine is employed in the prevention of Salmonellosis in water fowl. for example, the young of ducks and geese, at unfavourably affected farms. The vaccine is given to ducklings and goslings starting from the third day of life, being administered orally at a two days interval in a dose of 2 billion at the first, and 4 billion microbe cells at the second, feeding. Immunity is induced 3% days following administration of the second dose of the vaccine and is retained as long as six months.

Further illustrative of the invention are the following examples of making and testing the vaccine.

EXAMPLE 1

Preparation of a single series of the vaccine

This process for making the vaccine comprises the following steps:

obtainment of a growing culture. To this end, an ampoule containing desiccated attenuated strain *S. typhi-murium* No. 3 was emptied into two or three 100–200 $cm^3$ flasks with Hottinger's broth (culture volume one half of flask volume) accompanied by a control culture into the beakers containing meat-peptone agar, meat-peptone broth, meat-peptone liver broth under petroleum jelly. Cultivation was conducted for 14–16 hours at a temperature of 37° C. The culture was inspected for impurities by microscopic examination of the smears stained according to Gram's method. The pure culture was placed into 200 $cm^3$ flasks containing Hottinger's broth allowing 10 $cm^3$ of the culture per 100 $cm^3$ of the medium, and subjected to growth at a temperature of 37° C. for 14–16 hours. The number of flasks under cultivation was dependent upon the desired volume of the matrix culture. Control cultures were performed in a meat-peptone agar, meat-peptone broth, meat-peptone liver broth (MPA, MPB, MPLB) under petroleum jelly.

To obtain the matrix culture, the contents of one flask were transferred into a bottle containing 10 l of Hottinger's broth with simultaneous control culture in beakers with MPA, MPB, MPLB under petroleum jelly, and in Petri dishes containing Endo medium in order to avoid contamination by extraneous microflora.

The cultivation in the bottles was carried out for 10–12 hours at a temperature of 37° C. in an amount required for cultivation in the reactor. The thus obtained growth was used for cultivation in beakers containing culture mediums or in Petri dishes containing Endo medium, and also for microscopy and determination of the concentration of microorganisms according to the visual standard, said concentration expected to be at least 500 million microbe cells per 1 $cm^3$.

The growing culture, screened for absence of impurities, was placed in the reactor containing a sterile culture medium cooled to 38° C. to establish a proportion of 8–10% of culture to the overall medium volume while simultaneously adding 0.1% (by weight of dry substance) of 40% sterile glucose solution.

Cultivation in the reactor continued for 10–12 hours at a temperature of 37° C., the culture being constantly mixed (50 r.p.m.) and continuously aerated to produce enrichment of each liter of the culture medium in the proportion of 1:2 per minute.

While performing cultivation, a sample of culture was taken every 1–2 hours to ascertain pH, purity of growth and concentration of microbe cells. In the case of elevated pH during cultivation, the culture was added with 40% sterile glucose solution (0.1% by weight of dry substance). Cultivation process was terminated on reaching the stable stage when the living microbe count ceased to increase.

The thus obtained culture was cooled to 6°–8° C. and tested for impurities by microscopy and performing culture in beakers with MPA, MPB, MPLB under petroleum jelly or in dishes with Endo medium. The culture contained 30–40 billion microbe cells per 1 $cm^3$ according to the visual standard, had a pH value between 7.4 and 7.6, and agglutinated under the influence of monoreceptor "O" serums: 1, 4, 5, 12 and H-serums (i, 1, 2). Subsequent to cooling the pure broth culture was transferred via a sterile tubing for concentration in the supercentrifuge.

To maintain the sterility conditions, the rotor of the centrifuge was transferred into the manual compartment, wherein the cultivated bacterial mass was collected from the rotor into the previously weighed and sterilized three liter jars containing beads. Subsequently, each jar was weighed again, the difference of weight giving the actual amount by weight of the collected concentrated bacterial culture.

The thus collected bacterial culture was diluted in 18–20 liter bottles with a protective medium to a concentration of 100–120 billion microbe cells per 1 $cm^3$ according to the visual standard of opacity.

The protective medium was prepared by the following sequence of processes: boiling distilled or demineralized water was used to dissolve gelatin in the strength of 1.5–2%, whereupon it was added with 10% of saccharose, subjected to boiling for a maximum of 5–6 minutes, subsequently strained through a cloth filter and given a pH value of 7.6–7.8 by adding a 4% solution of caustic soda, and then sterilized at a temperature of 110° C. for 30 minutes. Subsequent to sterilization the protective medium was tested for sterility by subjecting it to culture in MPA, MPB, MPLB under petroleum jelly.

The microbic culture suspension thoroughly mixed with the protective medium was placed in sterile ampoules and stoppered with loose cotton tampons. While being dispensed the vaccine was continuously mixed. The vaccine containing ampoules were inserted into a magazine to be put under freeze-storage in the refrigerator at a temperature of −40°–50° C. for 8–14 hours.

Upon completion of freezing the vaccine containing ampoules were transferred into the sublimation device, wherein they were subjected to drying.

Completion of the drying process was marked by the attainment of the given terminal temperature of the cultivated material (25° C.), minimal pressure inside the chamber, said values being maintained the same over the final hours of drying. Activation of the shelf heating, vacuum pumps, and discharge of the dried vaccine were performed in compliance with the operating instructions attached to the sublimation unit.

Ampoules with the dried vaccine were sealed on a drum collector unit at a maximum pressure of 0.2 mm Hg. The sealed ampoules were tested macroscopically for the presence of foreign impurities, while the state of vacuum inside the ampoules was determined using the instruments of D'Arsonvalle's or Tesla's design. The ampoules were then designated with lables listing the name of substance and serial number.

The ampoule contained vaccine was subjected to the following tests:
appearance,
purity and culture pattern,
visual concentration per 1 cm$^3$,
living microbe cell count and number of vaccine doses per 1 cm$^3$,
moisture content in percent by weight,
solubility,
presence of vacuum in ampoules,
operational safety,
immunogenicity.

EXAMPLE 2

Laboratory test of the living vaccine. Safety of the vaccine was tested on 2-5 day old ducklings and goslings in subcutaneous administration using doses of 1,2,5,10 and 2,5,10,20 billion of microbe cells, respectively.

The survival time of the vaccine strain in the animal's body was determined by bacteriological investigation of the internal structures and tissues of the vaccinated birds conducted at an interval of 5-10 days for a period of 2 months subsequent to the inoculation.

The immunogenic properties of the vaccine were studied in subcutaneous, combined (subcutaneous and oral), as well as oral administration performed once or twice. In subcutaneous administration the vaccine was introduced in a dose of 2 billion, whereas in oral and combined mole 1 and 2 billion of microbe cells were given at two days interval.

The experiments showed that the live vaccine, whether given subcutaneously or twice orally in the above-mentioned doses, did not produce any untoward reaction in 2-5 days old ducklings and goslings, control slaughtering of the birds 5, 10, and 20 days following inoculation showed no evidence of pathological changes in the internal structures.

In oral technique of immunization, complete excretion of the microbe cells occurred by the 35th day in ducks, and by the 40th day in geese.

The results of experimental studies of immunogenic properties of the live vaccine in diverse modes of application as compared to the known killed vaccine were listed in Tables 2 and 3. As seen in Table 2, 15 days subsequent to inoculation with the live vaccine administered in any of the modes under study, the ducklings were rendered immune to a subcutaneous infection with the virulent strain S. typhi-murium in a dose of 3 $LD_{50}$, the coefficient of immunologic efficacy (CIE) being 100.

At the same time, a single oral vaccination conferred immunity of a somewhat lesser intensity than the twice repeated administration. Thus, for example, 15 days following inoculation consisting of a single administration, the CIE value was 100 in response to 3 $LD_{50}$ infection, and 80 and 60 after a lapse of 30 and 45 days, respectively, in response to 6 $LD_{50}$ infection with the virulent strain.

The killed vaccine exhibited considerably less potent immunogenic properties.

The vaccine immunogenic capacity in the experiments on young geese (Table 3) was also sufficiently pronounced. CIE value 15, 30, 45, 60 days following twice repeated oral vaccination was 80, 80, 73, 73, respectively, in response to 3 $LD_{50}$ infection with the virulent strain.

The corresponding indices for the killed vaccine were 48, 33, and 10.

EXAMPLE 3

A test of the live vaccine under the industrial conditions. An industrial trial series with the vaccine were carried out at the poultry farms adversely affected by salmonellosis. The inoculation was performed according to the above-mentioned scheme on a total number of 107,400 young ducks. The known killed vaccine, whose administration adhered to the appropriate instructions, was used for comparison.

The mean results of a series of three industrial trials were summarized in Table 4. Survival rate in the study groups inoculated with the live or killed vaccine was on the average 96.5% and 88%, respectively, whereas this value in the control group was 83%. The indices of weight gain in poultry were 42.7, 36.0, 34.8 g, respectively, while the costs per each 100 kg of weight gain were 4.5, 5.8, 6.6 feed units.

Differences of the immunogenic efficacy indices exhibited by the live and killed vaccines were statistically authenticated ($P < 0.01$).

The general industrial saving accrued from the prevention of mortality in poultry, increased weight gain, lower costs of feeding and medication.

TABLE 2

| | | | Infection subsequent to inoculation (day) | | | | | | | | |
|---|---|---|---|---|---|---|---|---|---|---|---|
| | | | 15 | | | 30 | | | 45 | | |
| Nos 1 | Vaccine 2 | Immunization technique 3 | number of birds 4 | infection dose 5 | CIE 6 | number of birds 7 | infection dose 8 | CIE 9 | number of birds 10 | infection dose 11 | CIE 12 |
| 2 | Vaccine of this invention | single subcutaneous | 20 | 3$LD_{50}$ | 100 | 30 | 10$LD_{50}$ | 100 | 30 | 15$LD_{50}$ | 100 |
| | | oral-subcutaneous | 20 | 3$LD_{50}$ | 100 | 30 | 10$LD_{50}$ | 100 | 35 | 15$LD_{50}$ | 100 |
| | | single oral | 20 | 3$LD_{50}$ | 100 | 25 | 3$LD_{50}$ | 80 | 30 | 6$LD_{50}$ | 60 |
| | | double oral | 20 | 3$LD_{50}$ | 100 | 30 | 10$LD_{50}$ | 100 | 35 | 15$LD_{50}$ | 100 |
| 3 | Known killed vaccine | double subcutaneous | 20 | 3$LD_{50}$ | 52 | 20 | 10$LD_{50}$ | 40 | 20 | 15$LD_{50}$ | 20 |
| | | double oral | 20 | 3$LD_{50}$ | 48 | 20 | 10$LD_{50}$ | 33 | 20 | 15$LD_{50}$ | 10 |

TABLE 2-continued

Immunogenic properties of the vaccine in ducklings

| Nos 1 | Vaccine 2 | Immunization technique 3 | \multicolumn{3}{c}{Infection subsequent to inoculation (day)} | | | | | |
|---|---|---|---|---|---|---|---|---|
| | | | \multicolumn{3}{c}{60} | | | \multicolumn{3}{c}{90} | | |
| | | | number of birds 13 | infection dose 14 | CIE 15 | number of birds 16 | infection dose 17 | CIE 18 |
| 4 | Control | | 10 | $3LD_{50}$ | — | 10 | $3LD_{50}$ | — |
| 2 | Vaccine of this invention | single subcutaneous | 20 | $3LD_{50}$ | 100 | 20 | $3LD_{50}$ | 100 |
| | | oral-subcutaneous | 20 | $3LD_{50}$ | 100 | 20 | $3LD_{50}$ | 100 |
| | | single oral | — | — | — | — | — | — |
| | | double oral | 20 | $3LD_{50}$ | 100 | 20 | $3LD_{50}$ | 100 |
| 3 | Known killed vaccine | double subcutaneous | — | — | — | — | — | — |
| | | double oral | — | — | — | — | — | — |
| 4 | Control | | 10 | $3LD_{50}$ | — | 10 | $3LD_{50}$ | — |

TABLE 3

Immunogenic properties of the vaccine in goslings

| Nos 1 | Vaccine 2 | Immunization technique 3 | \multicolumn{3}{c}{Infection subsequent to inoculation (day)} | | | | | | | | | |
|---|---|---|---|---|---|---|---|---|---|---|---|---|---|
| | | | \multicolumn{3}{c}{15} | \multicolumn{3}{c}{30} | \multicolumn{3}{c}{45} | \multicolumn{3}{c}{60} |
| | | | number of birds 4 | infection dose 5 | CIE 6 | number of birds 7 | infection dose 8 | CIE 9 | number of birds 10 | infection dose 11 | CIE 12 | number of birds 13 | infection dose 14 | CIE 15 |
| 2 | Vaccine of this invention | single subcutaneous | 10 | $3LD_{50}$ | 80 | 15 | $3LD_{50}$ | 60 | 15 | $3LD_{50}$ | 60 | 15 | $3LD_{50}$ | 60 |
| | | double oral | 10 | $3LD_{50}$ | 80 | 15 | $3LD_{50}$ | 80 | 15 | $3LD_{50}$ | 73 | 15 | $3LD_{50}$ | 73 |
| 3 | Known killed vaccine | double subcutaneous | 10 | $3LD_{50}$ | 30 | 15 | $3LD_{50}$ | 22 | 15 | $3LD_{50}$ | 12 | — | — | — |
| | | double oral | 10 | $3LD_{50}$ | 25 | 15 | $3LD_{50}$ | 20 | 15 | $3LD_{50}$ | 7 | — | — | — |
| 4 | Control | | 10 | $3LD_{50}$ | — | 10 | $3LD_{50}$ | — | 10 | $3LD_{50}$ | — | — | — | — |

TABLE 4

Results of industrial trials of the vaccine on ducklings (average of a series of three tests)

| Nos. 1 | Vaccine 2 | Immunization technique 3 | Number of ducklings under study 4 | Mortality number 5 | Mortality % 6 | Survival % 7 | Mean daily weight gain 8 | Feed consumption per each 100 kg of weight gain, feed units 9 |
|---|---|---|---|---|---|---|---|---|
| 2 | Live vaccine of this invention | double oral | 107400 | 3759 | 3,5 | 96,5 | 42,7 | 4,5 |
| 3 | Known killed vaccine | double subcutaneous | 3000 | 360 | 12 | 88,0 | 36,0 | 5,8 |
| 4 | Control | — | 34800 | 5916 | 17,0 | 83,0 | 34,8 | 6,6 |

We claim:

1. A live vaccine for the prevention of Salmonellosis which comprises a suspension of live attenuated strain *Salmonella typhi-murium* No. 3 and a biologically acceptable carrier.

2. The vaccine composition of claim 1 wherein the strain is from that deposited at the All-Union State Research Control Institute for Veterinary Preparations Decorated with the Order of the Red Banner of Labor Under No. 121.

3. The vaccine composition of claim 1 wherein the strain is capable of growing in a culture medium having a high content of Streptomycin.

4. The vaccine of claim 1 comprising a concentration of microbe cells of from $1 \times 10^{11}$ to $2 \times 10^7$ per cubic centimeter.

5. The vaccine of claim 4 comprising water and a concentration of microbe cells of from $4 \times 10^8$ to $2 \times 10^8$ per cubic centimeter.

6. The vaccine composition of claim 1 wherein the strain ferments glucose, maltose, mannitol, arabinose, sorbite, xylose producing acid and gas; forms $H_2S$ and does not ferment saccharose, lactose, raffinose.

7. The vaccine composition of claim 5 wherein the antigen structure agglutinates under the influence of monoreceptor "O" serums: 1,4,5,12 and H-serums: of the first phase (i) and second phase 1 and 2.

8. The vaccine of claim 1 which has been freeze dried.

9. The vaccine of claim 1 wherein the genome of said strain comprises two mutations.

10. The vaccine of claim 1 further comprising a protective medium to preserve viability of the microbe cells comprising the following composition in % by weight saccharose: 4–12.0,
gelatin: 0.6–3.0,
water: remaining in an amount of 1 cubic centimeter per 30–40 million living microbe cells.

11. A process for making a live vaccine for prevention of Salmonellosis in water fowl comprising cultivating a strain *Salmonella typhi-murium* No. 3 deposited at the All-Union State Research Control Institute of Veterinary Preparations, the USSR, Ministry of Agriculture as No. 121 in a culture medium containing a source of carbon, nitrogen, mineral salts and biologically active substances at a temperature of 37°–38° C. to produce the highest attainable accumulation of biomass, recovering said biomass and drying said biomass to obtain said vaccine.

12. The process of claim 11 wherein said biomass is mixed with a protective medium comprising, saccharose, gelatin and water in an amount of one cubic centimeter per 30–40 billion of live microbe cells.

13. A method for immunization of water fowl against salmonellosis which comprises administering to the fowl orally at a 2–3 day interval a first dose of $2\times10^9$ microbe cells of live attenuated strain *Salmonella typhi-murium* No. 3 in drinking water and a second dose of $4\times10^9$ microbe cells of live attenuated strain *Salmonella typhi-murium* No. 3 in drinking water.

* * * * *